United States Patent
Cengiz Çallioğlu et al.

(10) Patent No.: US 12,392,055 B2
(45) Date of Patent: Aug. 19, 2025

(54) PRODUCTION METHOD OF INNOVATIVE NANOFIBER MEDICAL TEXTILE MATERIAL WITH TRANSDERMAL-DRUG RELEASE PROPERTIES

(71) Applicant: SÜLEYMAN DEMİREL ÜNİVERSİTESİİDARİ VE MALİİŞLER DAİRE BAŞKANLIĞI GENELSEKRETERLIK, Isparta (TR)

(72) Inventors: Funda Cengiz Çallioğlu, Isparta (TR); Hülya Kesici Güler, Isparta (TR)

(73) Assignee: SÜLEYMAN DEMIREL ÜNIVERSITESI IDARI VE MALI ISLER DAIRE BASKANLIGI GENELSEKRETERLIK, Isparta (TR)

( * ) Notice: Subject to any disclaimer, the term of this patent is extended or adjusted under 35 U.S.C. 154(b) by 0 days.

(21) Appl. No.: 18/292,885

(22) PCT Filed: Nov. 15, 2022

(86) PCT No.: PCT/TR2022/051298
§ 371 (c)(1),
(2) Date: Jan. 26, 2024

(87) PCT Pub. No.: WO2023/086069
PCT Pub. Date: May 19, 2023

(65) Prior Publication Data
US 2024/0360593 A1    Oct. 31, 2024

(51) Int. Cl.
| | | |
|---|---|---|
| *D01D 5/00* | (2006.01) | |
| *A61K 9/70* | (2006.01) | |
| *A61K 31/7052* | (2006.01) | |
| *A61K 47/42* | (2017.01) | |
| *D01F 6/56* | (2006.01) | |
| *D06M 13/372* | (2006.01) | |
| *D06M 23/10* | (2006.01) | |
| *D06M 101/18* | (2006.01) | |

(52) U.S. Cl.
CPC ........ *D01D 5/0007* (2013.01); *A61K 9/7007* (2013.01); *A61K 9/7084* (2013.01); *A61K 31/7052* (2013.01); *A61K 47/42* (2013.01); *D01F 6/56* (2013.01); *D06M 13/372* (2013.01); *D06M 23/10* (2013.01); *D06M 2101/18* (2013.01); *D06M 2200/00* (2013.01); *D10B 2211/20* (2013.01); *D10B 2321/12* (2013.01); *D10B 2509/00* (2013.01)

(58) Field of Classification Search
CPC .......................................... D01D 5/0007–0092
See application file for complete search history.

(56) References Cited

U.S. PATENT DOCUMENTS

| | | |
|---|---|---|
| 2013/0280319 A1 | 10/2013 | Mathiowitz et al. |
| 2014/0128345 A1 | 5/2014 | Woodrow et al. |

FOREIGN PATENT DOCUMENTS

| | | |
|---|---|---|
| CN | 102137658 A | 7/2011 |

OTHER PUBLICATIONS

Funda Cengiz Çallioğlu (2013): Silindirli Elektro Lif Çekim Yöntemi ile Nano Lif Üretimi (The Production of Nanofiber by Roller Electrospinning Method), Tekstil ve Mühendis (Journal of Textiles and Engineer), 20: 91, 35-49. (Year: 2013).*

* cited by examiner

*Primary Examiner* — Atul P. Khare
(74) *Attorney, Agent, or Firm* — Fresh IP PLC; Clifford D. Hyra; Aubrey Y. Chen

(57) ABSTRACT

Disclosed herein is the production of medical textile material with nanofiber surface that has transdermal drug release properties and that is coated with azithromycin active substance by using needle electrospinning method and ultrasonic spray pyrolysis (USP) technique. Specifically disclosed is a nanofiber medical textile material production method that includes the steps of preparing polymer solutions containing PVP (polyvinylpyrrolidone) with a concentration of 12 wt % and GEL (gelatin) with a concentration of 0.72 wt %; determining solution properties such as conductivity, viscosity, and surface tension, producing nanofibers from prepared polymer solutions at by atmosphere-controlled horizontal needle fiber spinning (electrospinning) setup, obtaining PVP/GEL nanofibers after the fiber spinning process, thin film coating of the drug active substance on the obtained nanofibers, PVP/GEL nanofibers by the USP method, and cross-linking of both polymers to facilitate the final application processes of the drug-release material.

9 Claims, 10 Drawing Sheets

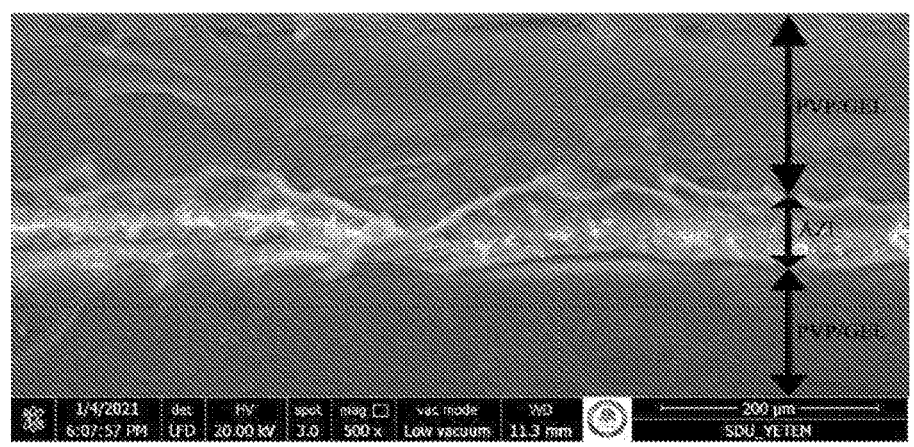
FIGURE 15-A
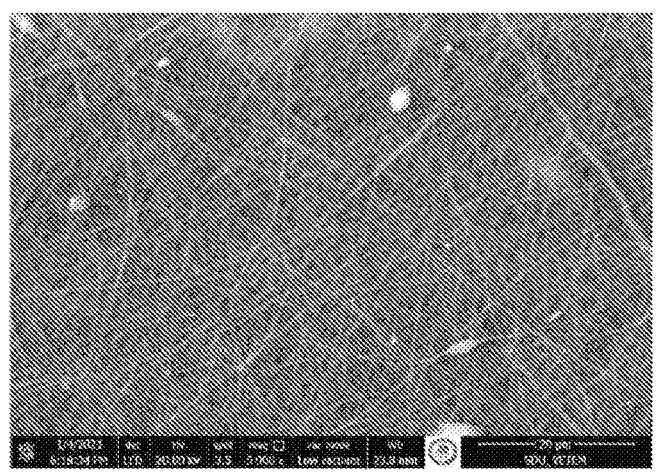
FIGURE 15-B
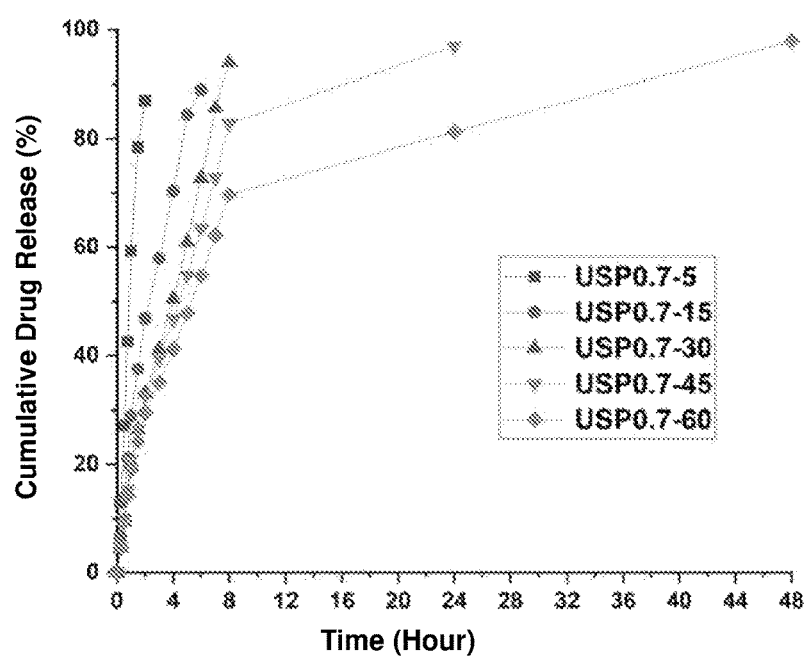
FIGURE 16

PRODUCTION METHOD OF INNOVATIVE NANOFIBER MEDICAL TEXTILE MATERIAL WITH TRANSDERMAL-DRUG RELEASE PROPERTIES

This application is a National Phase entry of International Application No. PCT/TR2022/051298 under § 371 and claims the benefit of Türkiye Patent Application No. 2021/017752, filed Nov. 15, 2021, which is hereby incorporated by reference in its entirety.

FIELD OF THE DISCLOSURE

The present disclosure relates to the production of medical textile material with nanofibrous surface, having transdermal drug release properties by using needle electrospinning method and ultrasonic spray pyrolysis (USP) technique.

The present disclosure relates more specifically to a medical textile manufacturing method capable of transdermal drug release comprising the processes of obtaining nanofibrous structure by using Polyvinylpyrrolidone (PVP) and Gelatin (GEL) polymers together with needle electrospinning method, adding AZI (azithromycin) active substance with drug loading to nanofibers by Ultra Spray Pyrolysis (USP) method.

BACKGROUND

Today, some inconveniences are encountered in the systemic administration of the drugs used. Especially for antibiotics, high oral doses are required and may develop resistance against bacterial varieties. Over time, due to this high dose, the resistance of bacteria to antibiotics makes treatment impossible.

By means of the transdermal drug delivery, this situation is eliminated, and the dose can be given as much as the patient needs without the need for high doses. When the state of the art was evaluated, commercially used transdermal drugs such as durogesic, exelon, and nicotinell were encountered.

Transdermal therapy systems or transdermal patches deliver drugs to the body through skin absorption. One advantage thereof is immediate visual confirmation of application when the patch is applied to the skin. In addition, formulas are designed to control the rate of drug absorption, which helps maintain drug-blood concentration over an extended period of time.

The plasma level of the drug can remain constant for the desired time by controlled release drug delivery systems. Thus, the patient avoids taking the drug too often and the treatment can be provided with very low doses. Since treatment can be provided with low doses in this way, side effects and toxic effects thereof are reduced or completely eliminated. By means of these systems, the frequency of giving drug to the patient is reduced, the risk of forgetting the drug is eliminated, and nighttime drug taking is eliminated. It is an important parameter especially in psychiatric patients, children, and elderly. In this case, the quality of life of patients increases and patient care becomes easier.

In the state of the art, different methods have been used in the production of transdermal drug delivery systems.

In the state of the art, there are many studies in the literature regarding the production of nanofibers by electrospinning method.

For example, in the publication titled "Nano Fiber Production by Roller Electro Spinning Method" given https://www.researchgate.net/publication/259479847_Silindirli_Elektro_Lif_Cekim_Yontemi_ile_Nano_Lif_Uretimi, which is encountered in the state of the art, a study using the roller electro fiber spinning method is given.

SUMMARY

The present disclosure relates to the production of medical textile material with nanofibers, having transdermal drug release properties by using electrospinning method and ultrasonic spray pyrolysis (USP) method, which is aimed to provide an alternative solution to this problem encountered in the state of the art.

The present disclosure describes differences in the process steps in the production of nanofibers in the electrospinning method and the combination of polyvinylpyrrolidone (PVP) and gelatin (GEL) polymers. In addition, no drug loading to nanofibers and addition of AZI active substance were found by the USP method.

The present disclosure describes a horizontal electrospinning method technique. In the roller electro spinning method, a roller rotating at a certain speed is used as the fiber spinning apparatus. In the production method, which is the subject of this application, a single nozzle is used and the Taylor cone, which is an important function for fiber drawing, is one. In the roller electrospinning method, tens of Taylor cones are formed simultaneously along the roller. In addition, while a voltage higher than 80 kV is used in the roller electrospinning method, a voltage of 25-30 kV is sufficient in needle electrospinning. As explained, the working principle of the two technologies is also quite different from each other.

The present disclosure relates to the production of medical textiles with nanofibrous surfaces by using the electrospinning method. With this method, nanofiber production can be carried out with many known polymer raw materials. USP (ultrasonic spray pyrolysis) method, which is another technique used in the present disclosure, is widely available in the literature on thin-film coating of inorganic materials on non-porous surfaces such as glass, metal, and film. However, in present disclosure, unlike the literature, the drug active substance is coated in a thin film layer on nanofiber surfaces with high porosity by ultrasonic spray pyrolysis (USP) method. In the present disclosure, an innovative medical textile was produced for the first time in terms of both technical aspects (process steps of the production method and coating of the active drug substance as a thin film layer) and the use of azithromycin drug active substance.

In addition, the inventor has surprisingly achieved the superior characterizing properties of the nanofiber medical textile material with transdermal drug release, produced by the new method he/she developed, after the studies carried out. Detailed characterization studies of nanofiber surfaces have also been completed and are given within the scope of the description.

An object of embodiments of the present invention is to develop a nanofiber structure with high specific surface area ($m^2/g$) and drug-loaded very thin fiber diameter, and having high loading capacity, high porosity, open and small pore structure. Products with superior properties have been developed compared to film structures. Conventional fibers have an average specific surface area of 0.2 $m^2/g$, while nanofibers have an average specific surface area of 200 $m^2/g$. While the linear density of conventional fibers is 1-30 dtex on average, the linear density of nanofibers is around 0.0001 dtex. While the diameter of conventional fibers is about 10-40 μm, the average fiber diameter of nanofibers is around 0.2 μm.

Another feature of embodiments of the present invention is that since the produced nanofibrous biomaterial has the property of transdermal drug delivery, other advantages of the drug compared to the systemic administration form (using low dosage, facilitating patient care, etc.) are also utilized.

In the present disclosure, a nanofibrous medical textile surface with azithromycin release feature, which is used as a model drug, has been developed. In the application of embodiments of the present invention, thin-film coating of broad-spectrum lipophilic antibiotic on nanofibers has been carried out in different sandwich structures and then the release behavior of the drug from the surfaces were determined. While producing nanofibers, optimization studies were carried out in terms of both polymer solution properties and process parameters. Then, detailed characterization studies of model drug coated nanofiber surfaces were carried out. With the findings obtained from the study, it was concluded that the nanofibrous material has an industrial level production and an important application potential in terms of biomedical applications.

An important advantage of embodiments of the present invention is that it has been clearly seen that undesirable reactions do not occur and the material contents (polymers, active substance, etc.) do not interact with each other during the application of the inventive production method. In other words, with this production method (coating with USP), the drug coating process on nanofibers has been carried out successfully and safely.

Another advantage of embodiments of the present invention is that with this method, both immediate and controlled-release drug release systems can be prepared.

In addition, while commercially used (Durogesic 100 mcg/hour, Durogesic 75 mcg/hour, Durogesic 50 mcg/hour, Durogesic 25 mcg/hour, Exelon 13.3 mg/24 hours, Exelon 9.5 mg/24 hours, Nicotinell 14 mg/24 hours, 7 mg/24 hours etc.) transdermal products are in film structure, the material of embodiments of the present invention comprises fibers with high porosity and very small fiber diameter.

Embodiment of the present invention include a production method of drug-loaded, PVP/GEL-based, nanofibrous medical textile surfaces that can provide transdermal drug delivery as burst or controlled release, and it comprises the following process steps:

a) preparing polymer solutions containing PVP (polyvinylpyrrolidone) with a concentration of 12 wt % and GEL (gelatin) with a concentration of 0.72 wt %,
b) producing nanofibers from prepared polymer solutions with atmosphere-controlled horizontal needle electrospinning set up,
c) performing cross-linking process in two steps to maintain the stability of the produced material in aqueous environments since both polymers are water soluble,
d) obtaining PVP/GEL nanofibers,
e) Coating the model drug as a thin film to the PVP/GEL nanofibers by using the USP (ultrasonic spray pyrolysis) method.

BRIEF DESCRIPTION OF THE FIGURES

FIG. 1 is an SEM image of PVP/GEL nanofibers coated with AZI with sample code USP0.1 (×5000 and ×20000), according to at least one embodiment of the present invention.

FIG. 2 is an SEM image of PVP/GEL nanofibers coated with AZI with sample code USP0.3 (×5000 and ×20000), according to at least one embodiment of the present invention.

FIG. 3 is an SEM image of PVP/GEL nanofibers coated with AZI with sample code USP0.5 (×5000 and ×20000), according to at least one embodiment of the present invention.

FIG. 4 is an SEM image of PVP/GEL nanofibers coated with AZI with sample code USP0.7 (×5000 and ×20000), according to at least one embodiment of the present invention.

FIG. 5 is an SEM image of PVP/GEL nanofibers coated with AZI with sample code USP0.9 (×5000 and ×20000), according to at least one embodiment of the present invention.

FIG. 6 is an SEM image of USP0 (without drug active substance (AZI)) nanofibers (×5000 and ×20000), according to at least one embodiment of the present invention.

FIG. 7 is a histogram of PVP/GEL (USP0) nanofibers, according to at least one embodiment of the present invention.

FIG. 8 is a FT-IR spectra of AZI, PVP, GEL and nanofibers, according to at least one embodiment of the present invention.

FIG. 9 shows TGA curves of powdered AZI, PVP, and GEL, according to at least one embodiment of the present invention.

FIG. 10 shows TGA curves of PVP/GEL based nanofibers coated with AZI at different concentrations by USP method, according to at least one embodiment of the present invention.

FIG. 11 shows DSC curves of powdered AZI, PVP and GEL, according to at least one embodiment of the present invention.

FIG. 12 shows DSC curves of PVP/GEL based nanofibers coated with AZI at different concentrations by USP method, according to at least one embodiment of the present invention.

FIG. 13 shows XRD diffractograms of pure AZI, PVP, GEL, and PVP/GEL nanofibers coated with different concentrations of AZI, according to at least one embodiment of the present invention.

FIG. 14 shows cumulative release profiles of PVP/GEL nanofibers coated with AZI at different concentrations, according to at least one embodiment of the present invention.

FIG. 15A is a cross-section SEM image of nano mesh structure in sandwich structure (×500), according to at least one embodiment of the present invention.

FIG. 15B is an SEM image of nano mesh structure in sandwich structure (×500), according to at least one embodiment of the present invention.

FIG. 16 shows cumulative drug release profiles of sandwich structures, according to at least one embodiment of the present invention.

FIG. 17 is a post-release SEM image of nanofiber surfaces coated with AZI with sample code USP0.1 (×10000), according to at least one embodiment of the present invention.

FIG. 18 is a post-release SEM image of nanofiber surfaces coated with AZI with sample code USP0.3 (×10000), according to at least one embodiment of the present invention.

FIG. 19 is a post-release SEM image of nanofiber surfaces coated with AZI with sample code USP0.5 (×10000), according to at least one embodiment of the present invention.

DETAILED DESCRIPTION

Figure 1:
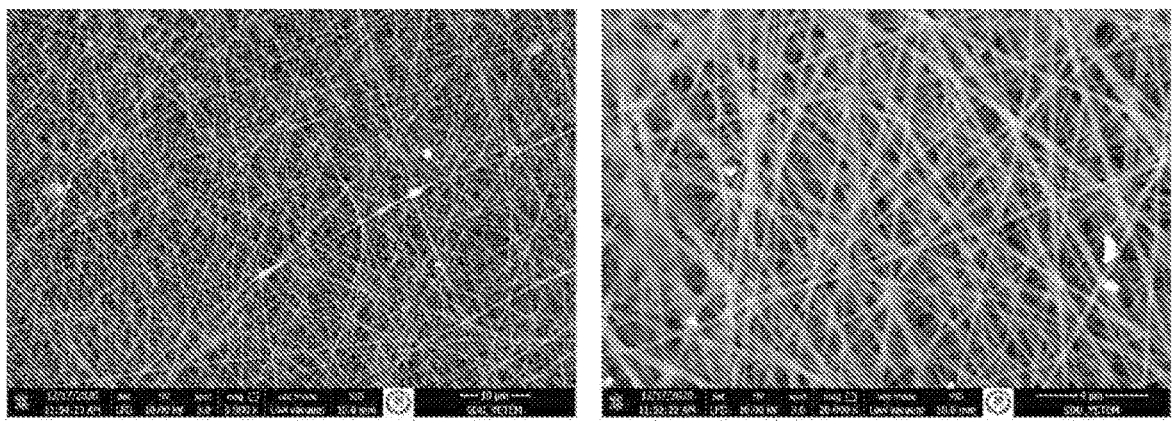
Figure 2:
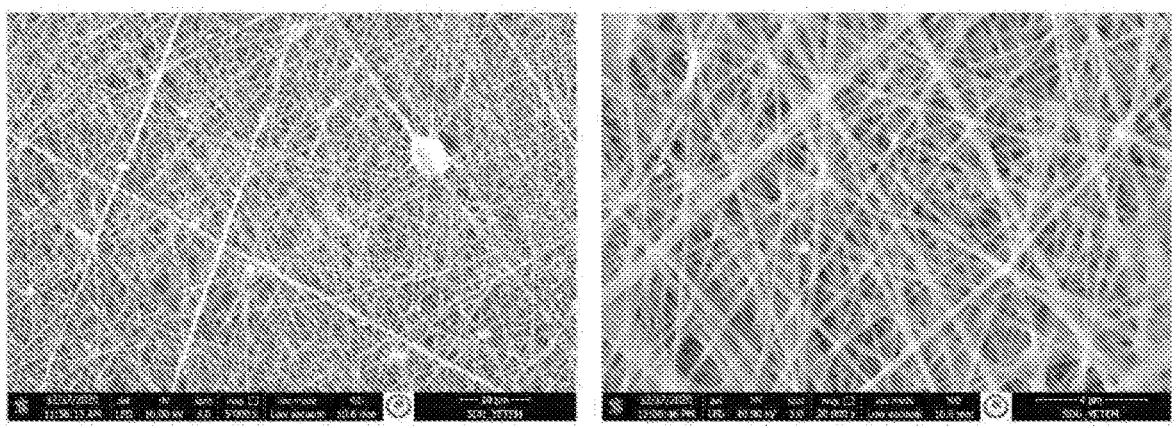
Figure 3:
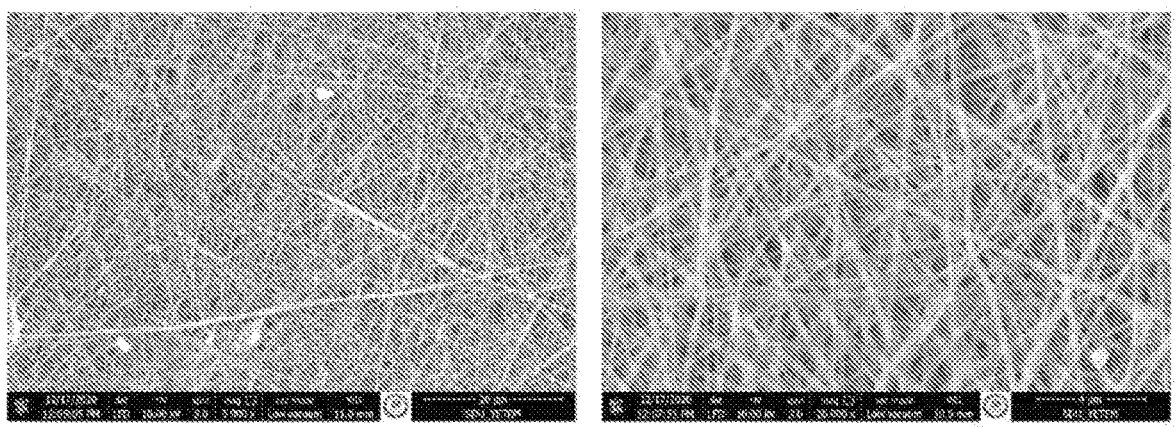
Figure 4:
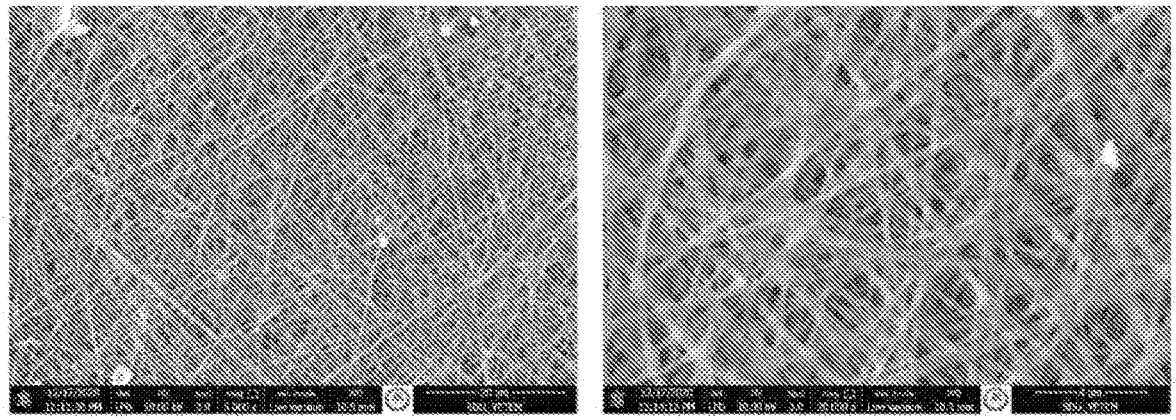
Figure 5:
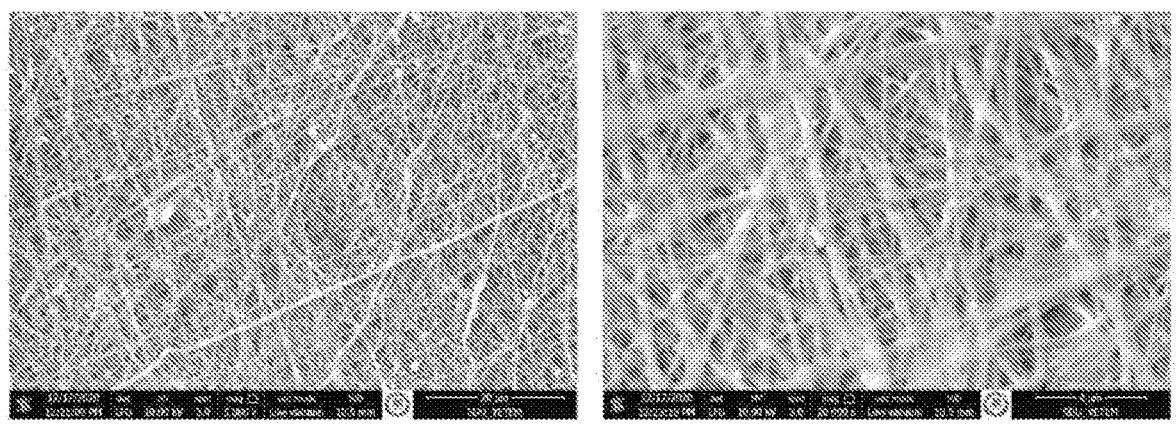
Figure 6:
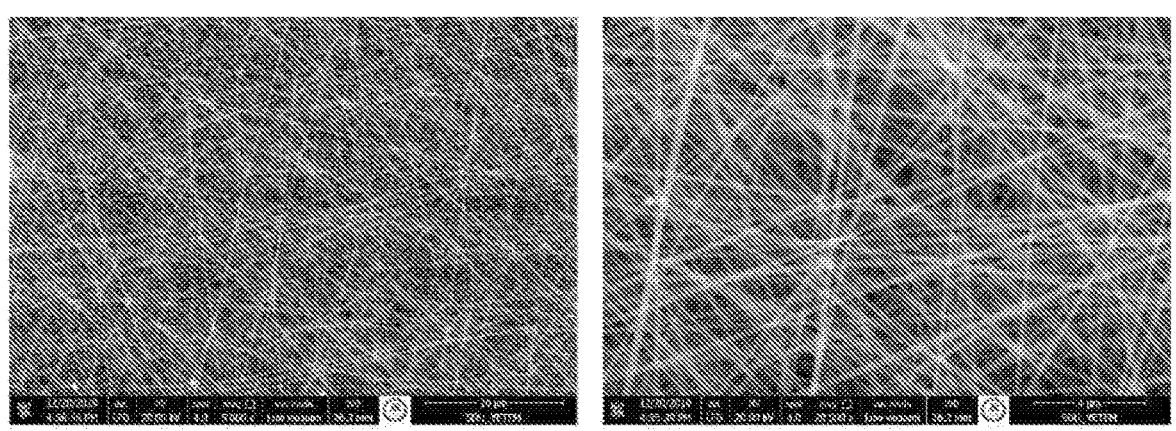

In the present disclosure, a nanofiber based medical textile surface with transdermal drug release properties was developed. Considering the 'green electrospinning' approach, polyvinylpyrrolidone (PVP) and gelatin polymers were used as raw materials, and ultrapure water and acetic acid were used as solvents due to the production of medical surfaces. For this purpose, the drug release behavior of the nanofibers was investigated by coating the surface of the nanofibers with the lipophilic antibiotic (azithromycin), ultrasonic spray pyrolysis (USP) method selected as the model drug. Firstly, polymer solution concentration optimization (polymer concentration, drug concentration, etc.) and then solution properties such as conductivity, surface tension and viscosity of polymer solutions were analyzed. In the production of drug-loaded nanofibers, optimization studies (such as voltage, distance between electrodes, solution feed rate and humidity) were completed in the electrospinning method and nanofibers with optimum properties were produced under the optimum process. Afterwards, optimization studies (under the temperature, nozzle frequency and distance etc.) were carried out with the ultrasonic spray pyrolysis method, which is another approach, and the PVP/GEL based nanofiber surface was coated with AZI. After the material production was completed, the characterization studies of the drug-loaded nanofibers were carried out by SEM, FTIR, XRD, DSC, TGA methods. Finally, by cross-linking the developed AZI loaded nanofibers, drug release behavior thereof was analyzed, and their release profiles were compared.

In the production method that is the subject of embodiments of the invention; it was aimed to produce drug-loaded PVP/GEL based nanofiber medical textile surfaces with optimum properties, to determine their drug release performance and to investigate their usability in transdermal drug delivery. For this purpose, first of all, polymer solutions were prepared. As a result of optimization studies within the scope of the study, polymer solutions were prepared with a PVP concentration of 12 wt % and a GEL concentration of 0.72 wt %. Then, solution properties such as conductivity, viscosity, and surface tension were measured. After the polymer solution properties were characterized, nanofiber production was carried out with an atmosphere-controlled horizontal needle electrospinning setup. Matsusada Precision Inc. (Kusatsu, Japan) was used as the power supplier and New Era Pump Systems (Farmingdale, NY, USA) was used as the solution feeding pump in the setup.

During fiber spinning, all solutions were produced in equal time with the same process parameters. The produced nanofibers were collected on aluminum foil. The optimum process parameters applied during fiber spinning are given in Table 1.

TABLE 1

| Electro fiber spinning process parameters | | | | | | |
|---|---|---|---|---|---|---|
| Voltage (kV) | Distance between electrodes (cm) | Feed rate (mL/h) | Humidity (%) | Temperature (° C.) | Needle Diameter (mm) | Production Time (minutes) |
| 26.4 | 17.0 | 0.3 | 33 ± 2 | 23.5 ± 1 | 0.8 | 60 |

The production method of drug-loaded, PVP/GEL-based, nanofiber medical textile surfaces that can provide transdermal drug delivery as burst or controlled release, which is a subject of embodiments of the present invention, comprises the following process steps:
 a) preparing polymer solutions containing PVP (polyvinylpyrrolidone) with a concentration of 12 wt % and GEL (gelatin) with a concentration of 0.72 wt %,
 b) producing nanofibers from prepared polymer solutions with atmosphere-controlled horizontal needle fiber spinning (electrospinning) set up,
 c) performing cross-linking process in two steps to maintain the stability of the produced material in aqueous environments since both polymers are water soluble,
 d) obtaining PVP/GEL nanofibers,
 e) Coating the drug active substance as a thin film on the obtained PVP/GEL nanofibers by the USP (ultrasonic spray pyrolysis) method.

Two-step cross linking process was performed on the nanofiber surfaces obtained after the electrospinning process. The cross linking process is performed to maintain the stability of the nanowebs in the aqueous environment and to increase their stability. In this study, these polymers were cross-linked in two steps since both polymers (PVP and GEL) used are water soluble. The first step of the cross linking process is the crosslinking of the PVP polymer. PVP polymer was heat crosslinked. As a result of the optimization studies carried out for the above-mentioned purpose, The optimum temperature was determined as 180° C. and the optimum time as 4 hours. In the second step, the GEL polymer was crosslinked. The GEL polymer was chemically cross linked and glutaraldehyde crosslinker was used for this. After the optimization studies, it was determined that the nanowebs were cross linked in glutaraldehyde vapor for 24 hours at room temperature. When the literature was analyzed, no study was found in which cross linking was carried out by using these two polymers together.

After cross linking, the nanowebs were coated with the drug by using the USP technique. Details of coating process are given below:

An important process step of the method of embodiments of the present invention is the thin film coating of the AZI active substance on the PVP/GEL nanofibers by using the USP method. This process was carried out with the Sono-Tek brand FlexiCoat model USP device in the Energy Technologies laboratory within the Innovative Technologies Application and Research Center of Süleyman Demirel University.

The AZI was first dissolved in chloroform to be used in the USP method. During the process, n-hexane was used as an anti-solvent to prevent the chloroform from dissolving the nanofiber surface and damaging it. The chloroform/n-hexane ratio was kept constant as ⅕ in the solution and the AZI concentration was adjusted to be 0.3 mg/mL. Then, optimization studies were carried out for USP to determine process parameters such as substrate temperature, solution flow rate, forming gas pressure, nozzle frequency, and distance. As a result of the optimization studies, the process parameters are given in Table 2.

TABLE 2

Process parameters of USP method

| Flow Rate (mL/minute) | Substrate temperature (° C.) | Distance between nozzle and substrate (cm) | Nozzle Frequency (kHz) | Forming (Nitrogen) gas Pressure (kPa) |
| --- | --- | --- | --- | --- |
| 1 | 100 | 13 | 85 | 1 |

In the next step, thin film coating process was performed on PVP/GEL (USP0) nanofibers with an appropriate amount of AZI/chloroform/n-hexane solution. In Table 3, the codes of the samples produced for this method and the amounts of AZI/chloroform/n-hexane solution used are given. In the study that is the subject of embodiments of the present invention, the amounts of AZI/chloroform/n-hexane solution coated were between 942 and 8460 μL.

TABLE 3

Sample codes and solution amounts used in the USP method

| Sample Code | Amount of Coated AZI Solution (μL) |
| --- | --- |
| USP0.1 | 942 |
| USP0.3 | 2826 |
| USP0.5 | 4716 |
| USP0.7 | 6600 |
| USP0.9 | 8460 |

After produced drug-loaded nanofiber surfaces, detailed characterization studies were carried out.

Figure 7:
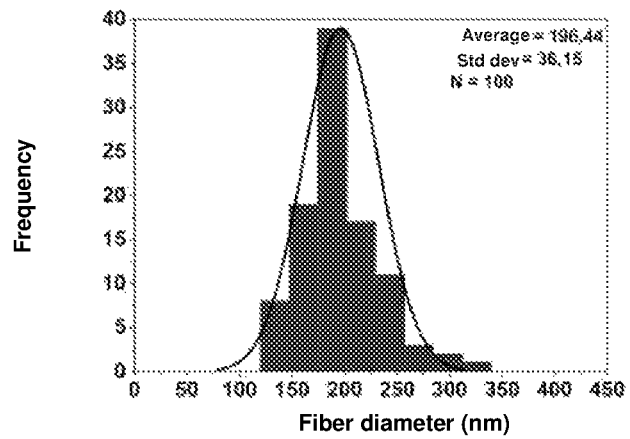

In FIGS. 1-5, SEM images of PVP/GEL nanofibers coated with different ratios of AZI by USP technique were provided. When SEM images are analyzed, first of all, with the increasing amount of coating, the AZI drug active substance is clearly seen on the surface of the nanowebs. As expected, the deformation of the surface increased with increasing coating time. In general, nanofibers have fine and uniform structure. FIG. 7 illustrates the histogram curve the fiber diameter distribution of USP0 (PVP/GEL) nanofibers.

According to FIG. 7, the average fiber diameter is 196.44 nm, and the standard deviation is 36.15 nm. The fiber diameter uniformity coefficient is 1.0335, and the fiber diameter distribution is homogeneous, and the normal distribution curve is unimodal. While the finest fiber in the nano-mesh structure was 128 nm, the thickest fiber was measured as 324 nm.

Figure 8:
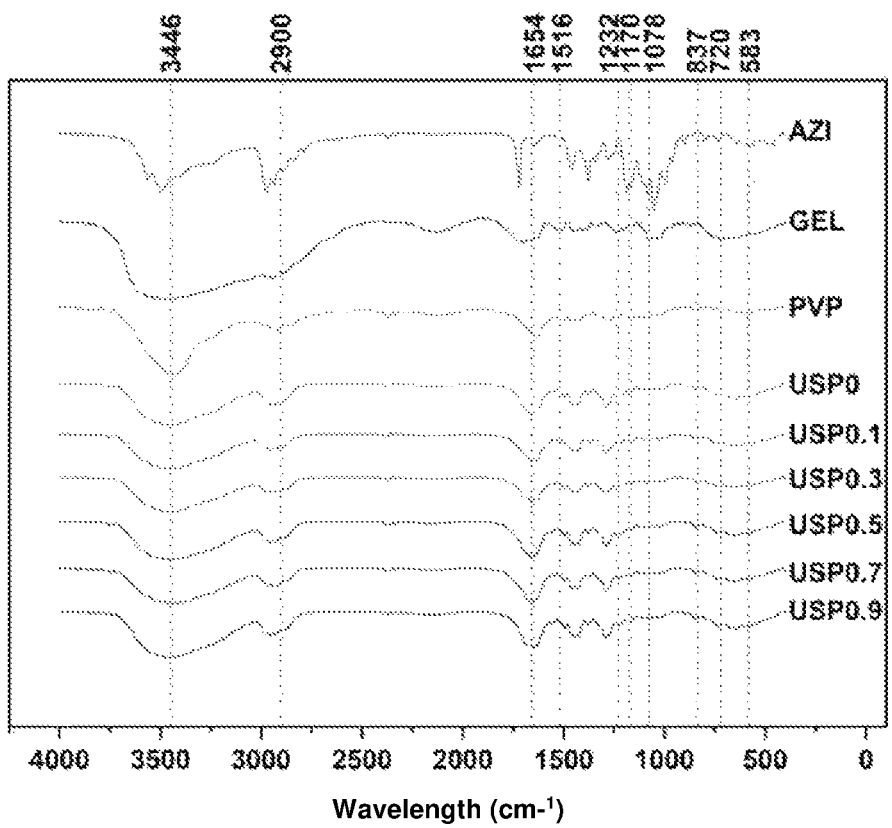

The FT-IR analysis performed with coated and pure nanofiber surfaces are given in FIG. 8.

When the spectra are analyzed in detail; the peak seen in the PVP spectrum at a wavelength of 3434 $cm^{-1}$ is the O—H stretching peak of the hydroxyl group. The alcohol O—H stretching vibration seen here at around 3600 $cm^{-1}$ is masked by a broad O—H peak of water molecules absorbed onto the PVP polymer. When the spectra of nanofibers coated by the USP technique are examined in detail; the O—H stretching peak of the hydroxyl group seen in the PVP spectrum at a wavelength of 3434 $cm^{-1}$ is 3446 $cm^{-1}$ in the USP0 sample, 3446 $cm^{-1}$ in the USP0.1 sample, 3446 $cm^{-1}$ in the USP0.3 sample, 3446 $cm^{-1}$ in the USP0.5 sample, 3447 $cm^{-1}$ in USP0.7 sample, and 3445 $cm^{-1}$ in USP0.9 sample. The presence of heteromeric molecules and carbonyl groups in the pyrrolidone ring of PVP was identified by the sharp peak at 1654 $cm^{-1}$ as a sign of C═O stretching. Here, the vibrational frequency of the carbonyl stretch is very sensitive to hydrogen bond formation with water molecules. Therefore, as the concentration of absorbed water increases, this peak may shift from 1680 $cm^{-1}$ to 1652 $cm^{-1}$. C—N stretching observed in the PVP spectrum at a wavelength of 1499 $cm^{-1}$ occur in USP0, USP0.1, USP0.3, USP0.5, USP0.7, and USP0.9, respectively, at a wavelength of 1494 $cm^{-1}$, 1495 $cm^{-1}$, 1494 $cm^{-1}$, 1495 $cm^{-1}$, 1495 $cm^{-1}$, and 1495 $cm^{-1}$ in nanofiber samples. In addition, the peak appearing at 1460 $cm^{-1}$ wavelength in the PVP spectrum can be attributed as the C—H distortion deformation of the $CH_2$ group, and this peak was detected at 1460 $cm^{-1}$ and 1462 $cm^{-1}$ wavelengths in all nanofiber samples. Moreover, $CH_2$ folding detected at 1165 $cm^{-1}$, C—C ring seen at 837 $cm^{-1}$ in the fingerprint region and N—C═O bending peak at 583 $cm^{-1}$ were also seen in the spectra of all nanofiber samples. Generally speaking, the presence of the heteroatom and carbonyl group in the pyrrolidone ring reduces the symmetry sufficiently. Therefore, most of the vibrational modes exist at different densities in the IR spectra of both PVP and PVP-based nanofibers.

The characteristic amide-I (C═O stretching), amide-II (N—H bending and C—H stretching), and amide-III (C—N stretching) peaks seen prominently in the GEL spectrum at wavelengths of 1456 $cm^{-1}$, 1516 $cm^{-1}$, and 1232 $cm^{-1}$, respectively appear in the spectra of nanofibers around these wavelengths, having lost their density. It is thought that the reason for losing their density is due to the use of low concentrations during the production of nanofibers. In addition, a weak peak was observed in the GEL spectrum at a wavelength of 720 $cm^{-1}$. This may be attributed to the —$CH_2$— rocking vibration seen in samples with 4 or more consecutive $CH_2$ groups, as in the amino acid lysine, which is an important component of gelatin.

The OH stretching peak seen at 3495 $cm^{-1}$ and 3562 $cm^{-1}$ wavelengths in the AZI spectrum is due to tightly bound water molecules in the AZI crystal lattice. In addition, other researchers have stated that the case where the double peak seen around the wavelength of 3500 $cm^{-1}$ falls into a single broad peak in the nanofiber spectra can be explained by the transition of AZI from crystalline form to amorphous form. Already in the DSC and XRD analyzes carried out within the scope of the study, it was determined that AZI transformed from crystalline form to amorphous form. Moreover, group peaks of OH group bending are also seen around 1458 cm$^{-1}$ wavelength in the AZI spectrum. The density of the C—O ether stretching peak seen in the AZI spectrum at a wavelength of 1188 cm$^{-1}$ increased from USP0.1 to USP0.9 in the nanofiber spectra, except for the USP0 sample, and appeared at wavelengths of 1169 cm$^{-1}$, 1170 cm$^{-1}$, and 1171 cm$^{-1}$. Also, the symmetrical aliphatic ether peak detected at 1051 cm$^{-1}$ in the AZI spectrum was around 1078 cm$^{-1}$ wavelength, not near the cm$^{-1}$ cm$^{-1}$ wavelength in the spectra of nanofibers, except for the USP0 sample. This may be due to the Van der Waals forces formed between the AZI and the carrier, namely the polymers. From the FT-IR spectra, it was determined that in general, no undesirable chemical interaction was observed between drugs and polymers, and the basic characteristic peaks of AZI and polymers were clearly seen in the nanofiber spectra.

Figure 9:
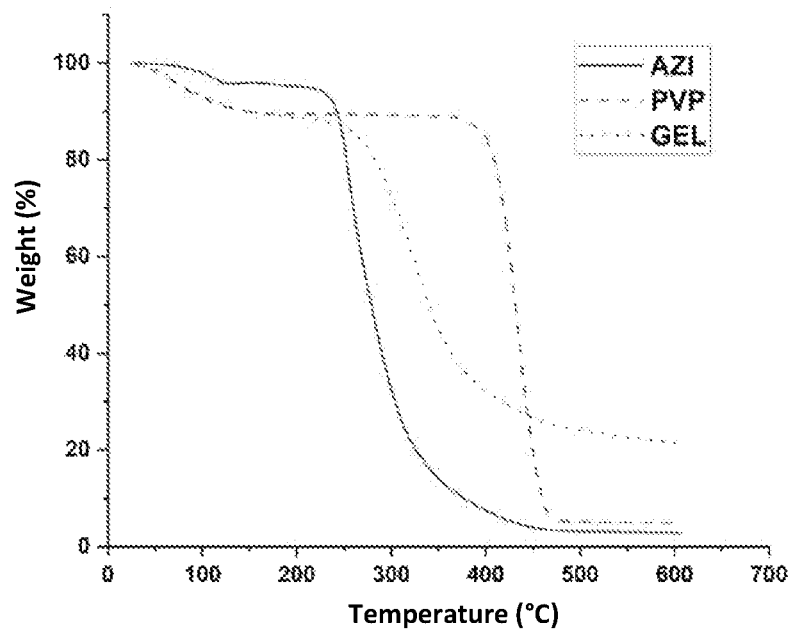

TGA analysis was carried out to determine the thermal stability of the model drug AZI, PVP and GEL polymers, and produced nanofibers used in the study. In FIG. 9, there are TGA thermograms of powdered form of AZI drug active substance and PVP and GEL polymers.

When FIG. 9 is examined in detail, it is clearly seen that AZI, PVP, and GEL show a one-step degradation. Due to the highly hydrophilic nature of PVP and GEL polymers, they lost 11.40% and 11.52% in weight, respectively, up to 100° C. due to the water molecules thereon. The PVP polymer degraded between 354.60° C. ($t_0$) and 478.10° C. ($t_f$), and left a residue of 5.72% at 600° C. Similarly, The GEL polymer, on the other hand, degraded with a weight loss of 63.14% between 221.73° C. and 469.76° C., and the sample had a mass of 25.34 wt % at the final temperature. Here, the GEL polymer rapidly realized 44.38 wt % loss at 352.10° C., while the remaining 18.76 wt % continued slowly up to 600° C. The 5.17 wt % loss of AZI between 25-120° C. indicates the transition of AZI from dihydrate to anhydrous AZI form. This observed 5.17 wt % loss corresponded to the stoichiometric weight loss of two water molecules.

The degradation temperature of AZI starts at 216.56° C., similar to the GEL polymer, and continues up to 472.30° C. Meanwhile, it lost 91.46% mass and left a very low amount of residue, such as 3.37%, at the final temperature of 600° C. (Table 4).

TABLE 4

Thermal degradation temperatures and residue amounts for PVP, GEL, and AZI

| Sample Name | $t_0$ (° C.) | $t_{max}$ (° C.) | $t_f$ (° C.) | Residue at 600° C. (%) |
|---|---|---|---|---|
| PVP | 354.60 | 433.04 | 478.10 | 5.72 |
| GEL | 221.73 | 328.39 | 469.76 | 25.34 |
| AZI | 216.56 | 280.14 | 473.30 | 3.37 |

Figure 10:
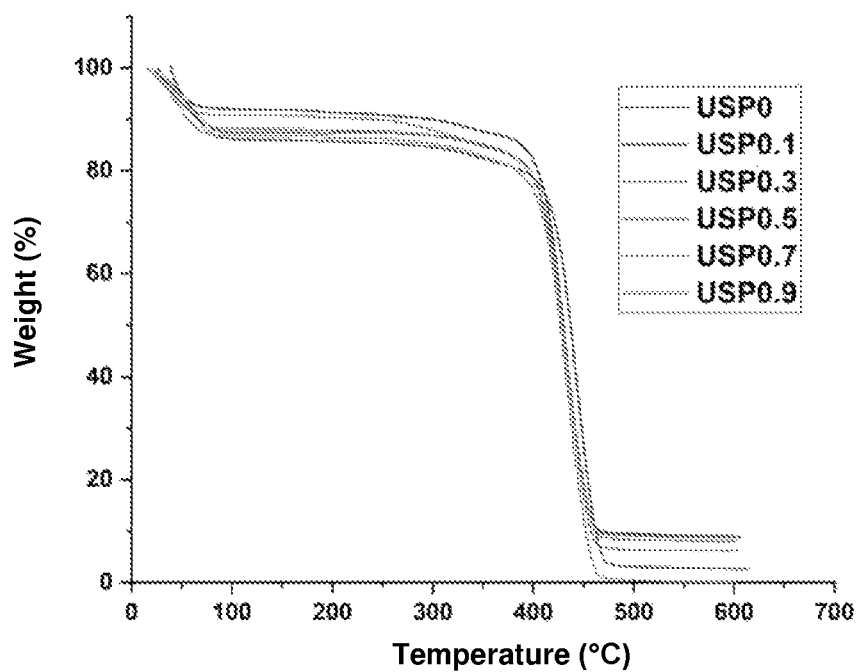

TGA thermograms of PVP/GEL nanofibers coated with AZI at different concentrations with the USP technique are provided in FIG. 10.

According to FIG. 10, weight loss was observed between 25-100° C. in all nanofiber samples due to the water molecules in their structures. In general, the temperatures at which nanofibers begin to degrade are between 306.9° C. and 354.1° C. Similarly, the temperature at which the mass loss ends is very close to each other and all samples are around 469° C. The amount of residue left by the samples varies between 0.010 mg and 0.383 mg. From the thermograms, it was observed that the degradation temperatures of nanofibers were higher than that of AZI and polymers (PVP and GEL). This situation can be attributed to some weak bond (Van der Waals) formation between polymers and active substance, as indicated in the FT-IR analysis. Therefore, this indicates that the AZI active substance has been successfully added to the structure of PVP/GEL nanofibers.

Finally, it can be said that the thermal stability of the AZI drug active substance is increased with the production of nanofibers since the degradation temperature of PVP is approximately 158° C. higher than that of AZI, and the degradation temperature of nanofibers is higher than that of PVP.

DSC thermograms show the change in heat flow within the sample as a function of increasing temperature. In addition, these thermograms indicate drug and polymer degradation and endotherms below 100° C., namely dehydration. Within the scope of the study, DSC and XRD analyzes were carried out to determine the physical state of the active substance, AZI, and molecular components in the fibers.

Figure 11:
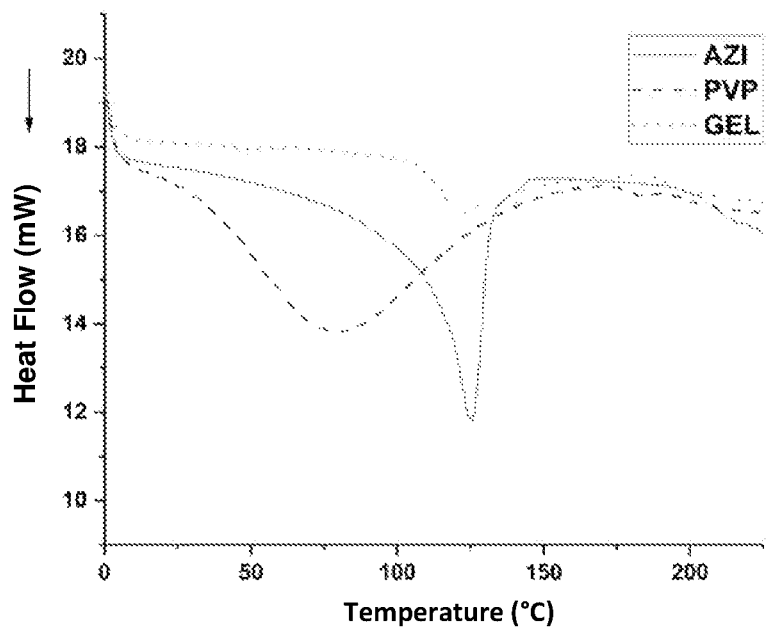

DSC thermograms of plain AZI, PVP, and GEL powders are provided in FIG. 11.

PVP, an amorphous polymer, shows a fairly large endotherm due to dehydration, extending from 29.73° C. to 137.57° C., reaching its maximum at 78.90° C. This observed peak is expected due to the hygroscopic and amorphous nature of PVP and is due to the water loss of the sample. As the materials become amorphous, the peak indicating the melting point ($t_m$) may disappear. It is known that the PVP polymer is predominantly amorphous. Also, the PVP polymer is a polymer that can be found in a glassy or rubbery form. Therefore, the corresponding $t_m$ peak is quite small. As seen in the DSC thermogram of PVP, A small endotherm is observed extending between 174.39-190.25° C., with a peak at 182.51° C. belonging to the $t_m$ point.

A very small endothermic transition, known as the softening temperature of the GEL polymer, was detected at 49.10° C. in the thermogram of pure GEL in powder form. Then, an endotherm peak is observed, starting at 111.58° C., peaking at 120.30° C., and ending at 130.28° C. At this temperature, the triple helix structure of GEL melts and randomly distributed structures are formed. The resulting enthalpy (ΔH) of transition with the value of 17.68 J/g represents the energy required to rearrange hydrogen bonds, amide bonds, and Van der Waals interactions into a random configuration that helps maintain the triple helical structure. This is very common for solid GEL, which always contains some water (normally 10-15%). Also, a small endothermic peak at about 213° C., known as the decomposition temperature of the plain GEL polymer powder, appeared as is known from the literature. This peak is in agreement with the TGA results.

A sharp endothermic peak is observed between 112.92-131.52° C., corresponding to the melting point, on the DSC thermogram of the AZI drug active substance. This wide endotherm peaked at 125.74° C. and the reason why the peak is wide is due to the separation of crystalline water in its structure during melting, as reported in the literature. The melting temperature for this peak was determined as 88.53 J/g. In the literature, different researchers have reported that AZI specimens exhibit variable thermal behavior with one or two DSC endotherms, while the United States Pharmacopeia reference standard has shown it with a single DSC endotherm.

Figure 12:
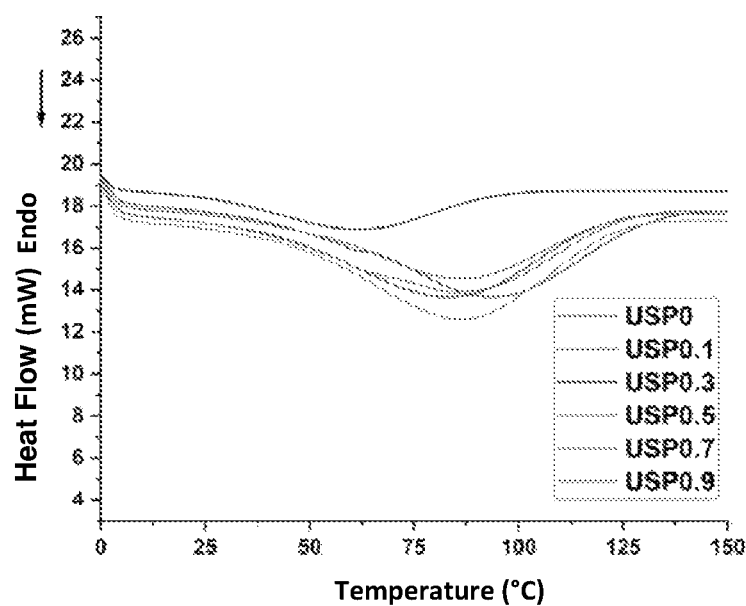

In FIG. 12, DSC thermograms of PVP/GEL nanofibers coated with AZI at different rates with the USP technique are provided.

When the DSC thermograms of nanofibers are examined in detail, It was clearly seen that AZI, which is the active substance of the drug, did not show any melting peak. This indicates that AZI no longer exists as a crystalline material, but has transformed into an amorphous state. This indicates that AZI has good compatibility with the polymer solution, good dispersion occurs when the drug and polymer solution are mixed, and high quality fibers are produced at the end of the electrospinning process. The obtained SEM images confirm this result concluded.

The endotherm peaks of nanofibers coated with thin film with different concentrations of AZI active substance vary between approximately 83° C. and 96° C., while endotherm was detected around 62° C. in the thermogram of PVP/GEL nanofibers without AZI. From this, it was determined that AZI coating on nanofiber surfaces with the USP technique causes an average of 20 to 25° C. shift in the endotherms of nanofibers.

Figure 13:
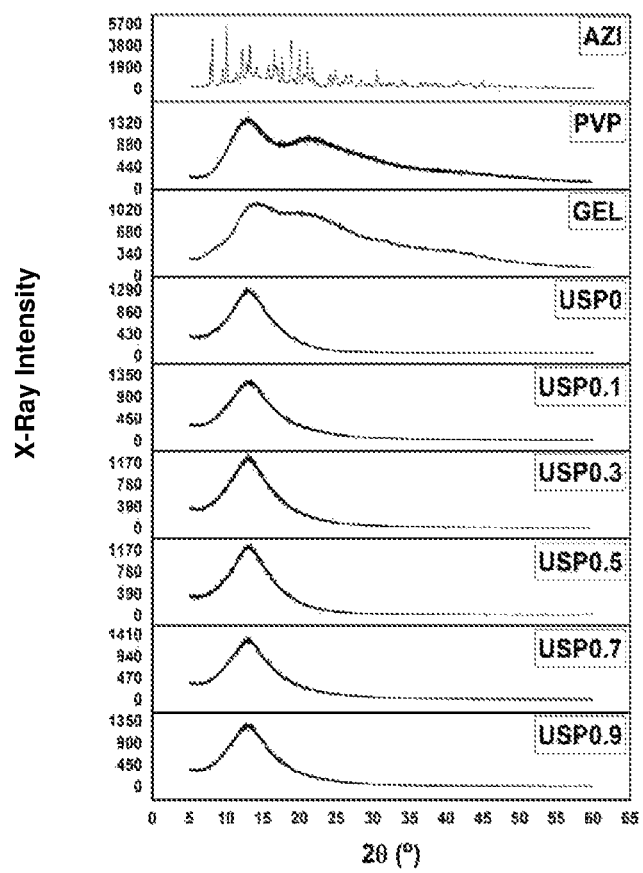

In FIG. 13, XRD curves of PVP/GEL nanofibers coated with different concentrations of AZI with pure AZI, PVP, GEL and USP technique are provided.

According to FIG. 13, in the XRD diffractogram of the pure AZI dihydrate sample, sharp peaks with different intensities appeared at the diffraction angles of 8.16°, 9.50°, 10.09°, 11.41°, 12.19°, 13.24°, 15.19°, 16.59°, 17.68°, 18.91°, 19.99°, 21.10°, 24.19°, 26.30°, 28.42°, 30.53° at 2θ due to its crystal structure. In addition, because of its crystal structure, AZI dihydrate has a complex XRD diffractogram with many diffraction peaks, while AZI monohydrate shows an amorphous structure. The diffraction pattern of the PVP polymer revealed a highly amorphous structure, as expected and well known from the literature. There are only two characteristic broad mounds in the spectrum at 12.86° and 21.37° between the Bragg angle of 10° and 25°. These mounds are due to the amorphous nature of the polymer, revealing that the molecular orientation of the polymer is irregular and complex. Similarly, there is a typical GEL XRD structure pattern originating from the α-helix and triple helix structure at 14.36° and 20.45° in the X-ray spectrum of the plain GEL polymer powder.

A broad and diffuse mound-shaped peak appeared in all samples under X-ray diffraction of Nano Fibers. These mound-shaped peaks are due to the amorphous polymers in the structure of nanofibers and appear around 13° in all diffractograms of nanofibers. The characteristic peaks of AZI are almost absent in the diffractogram of electrospun nanofibers. This made it clear that AZI no longer exists as a crystalline material but has been completely converted to an amorphous state.

DSC and XRD data of USP coated nanofibers proved that drug molecules are in an amorphous state in the matrix of PVP/GEL nanofibers. The XRD, DSC results obtained at this stage of the study and the SEM images in which the morphological observations were made overlap both with each other and with the previous studies involving electro-pulled nanofibers.

As can be seen in the figures and graphics, the analysis results given in detail above, first of all, the morphological, chemical and thermal properties of the material obtained with the analyzes were determined and analyzed in detail. As a result of these analyzes, it was clearly seen that undesirable reactions did not occur during production and that the material contents (polymers, active substance, etc.) did not interact with each other. In other words, with this production method (coating with USP), the drug coating process on nanofibers has been carried out successfully. In addition, with this method, both immediate and long-release drug release systems can be prepared. In addition, while commercially used (Durogesic 100 mcg/hour, Durogesic 75 mcg/hour, Durogesic 50 mcg/hour, Durogesic 25 mcg/hour, Exelon 13.3 mg/24 hours, Exelon 9.5 mg/24 hours, Nicotinell 14 mg/24 hours, 7 mg/24 hours etc.) transdermal products are in film form, the material of embodiments of the present invention comprises fibers with nano-sized pores and diameters. By means of this material, superior properties of nanofibers such as high specific surface area (conventional fibers have an average specific surface area of 0.2 $m^2/g$, while nanofibers have an average specific surface area of 20 $m^2/g$), nano-sized fiber diameter (the diameter of conventional fibers is about 10-40 μm, while the average fiber diameter of nanofibers is around 0.2 μm), high porosity, adjustable pore size and open pore structure, high loading capacity, high linear density (linear density of conventional fibers is on average 1-30 dtex, while linear density of nanofibers is around 0.0001 dtex) were utilized.

In addition, the drug release behavior and release performance of the medical textile material produced by the production method of embodiments of the present invention was supported by comparative data.

In Table 5, the diameter, weight, thickness information, and loading effect values measured before the release studies of nano-nets coated with different amounts of AZI by the USP method are provided.

TABLE 51

Diameter, weight, thickness, and loading effect values of nano meshes coated with USP

| Sample Code | Nano mesh diameter (mm) | Nano mesh thickness (μm) | Nano mesh weight (mg) | Loading effect (%) |
|---|---|---|---|---|
| USP0.1 | 51 | 332.3 | 45.2 | 80 |
| USP0.3 | 53 | 327.1 | 44.5 | 84 |
| USP0.5 | 55 | 364.8 | 45.5 | 88 |
| USP0.7 | 54 | 352.9 | 43.0 | 92 |
| USP0.9 | 52 | 374.3 | 43.5 | 94 |

Figure 14:
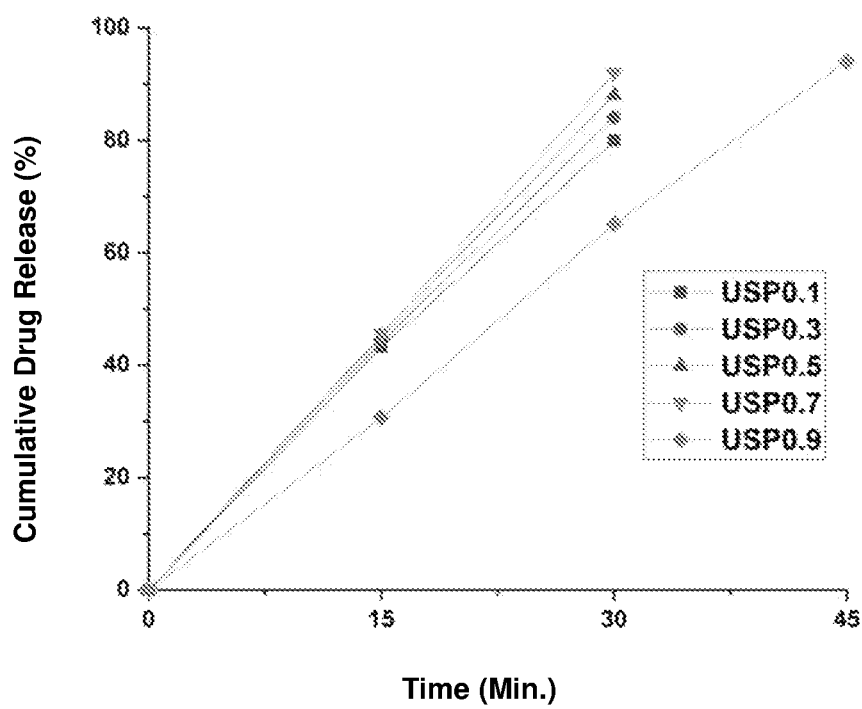
Figure 17:
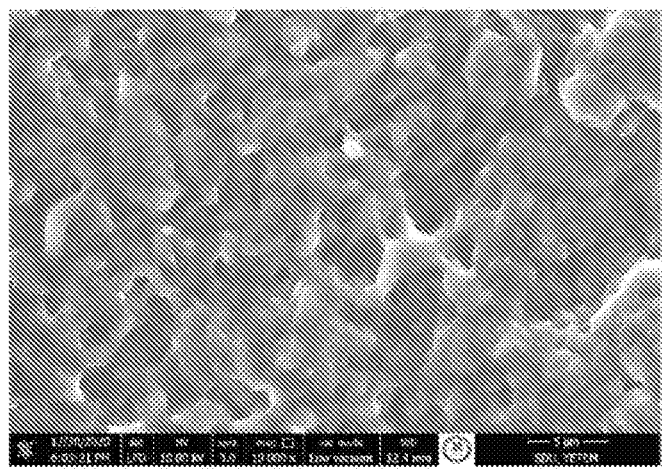
Figure 18:
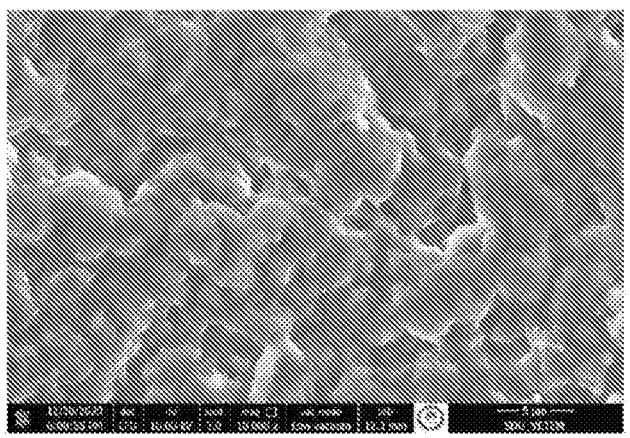
Figure 19:
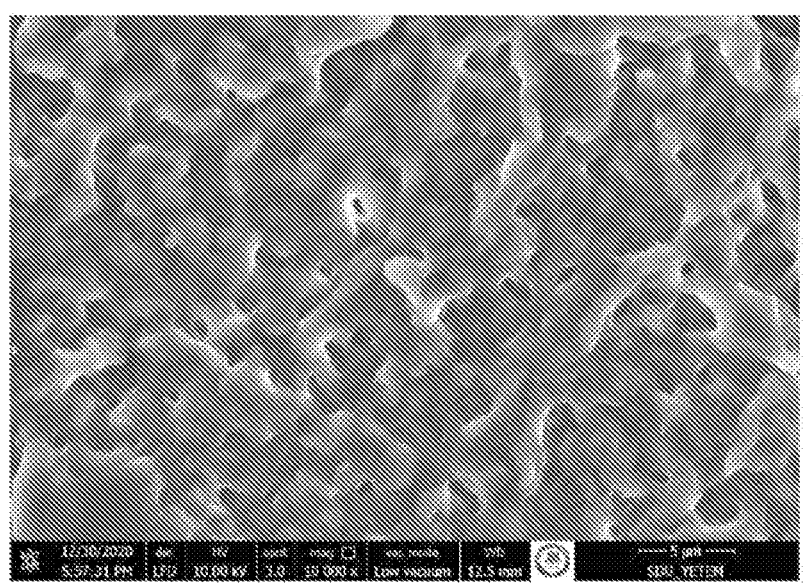
Figure 20:
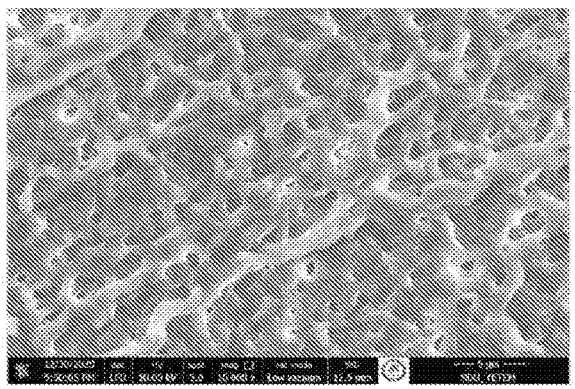
FIG. 20 is a post-release SEM image of nanofiber surfaces coated with AZI with sample code USP0.7 (×10000), according to at least one embodiment of the present invention.
Figure 21:
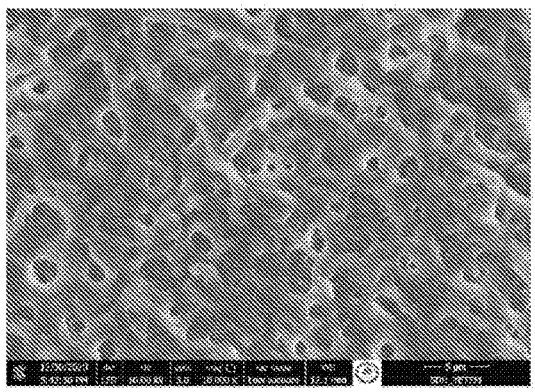
FIG. 21 is a post-release SEM image of nanofiber surfaces coated with AZI with sample code USP0.9 (×10000), according to at least one embodiment of the present invention.
Figure 22:
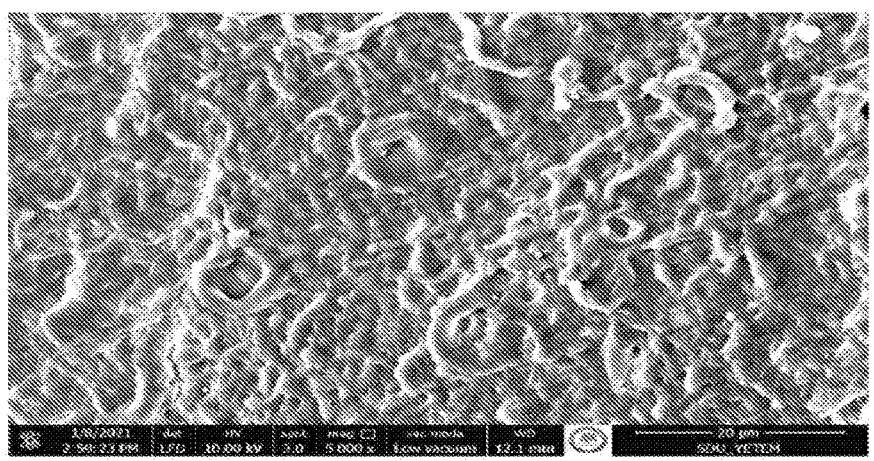
FIG. 22 is an SEM image of sandwich structures after release study for sample USP0.7-5 (×5000), according to at least one embodiment of the present invention.
Figure 23:
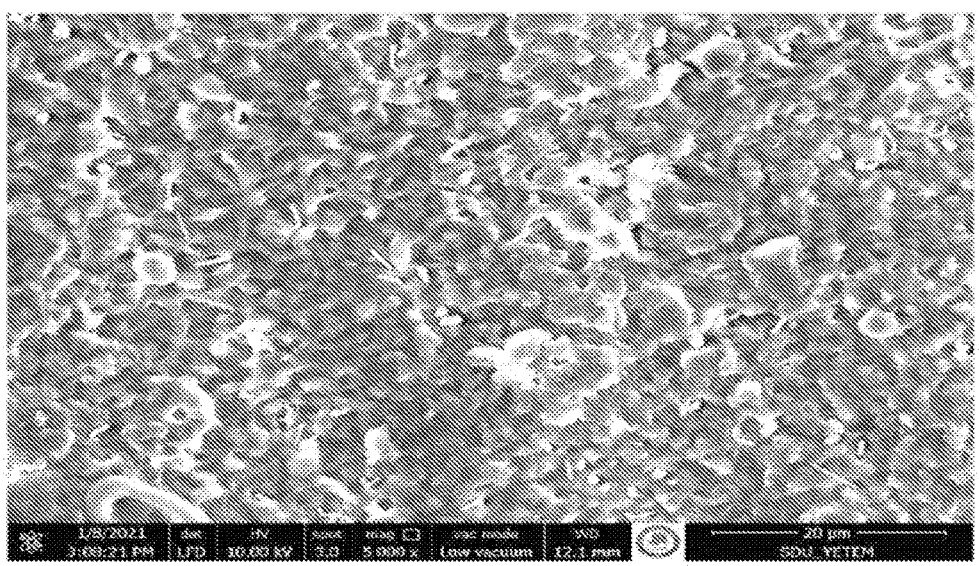
FIG. 23 is an SEM image of sandwich structures after release study for sample USP0.7-15 (×5000), according to at least one embodiment of the present invention.
Figure 24:
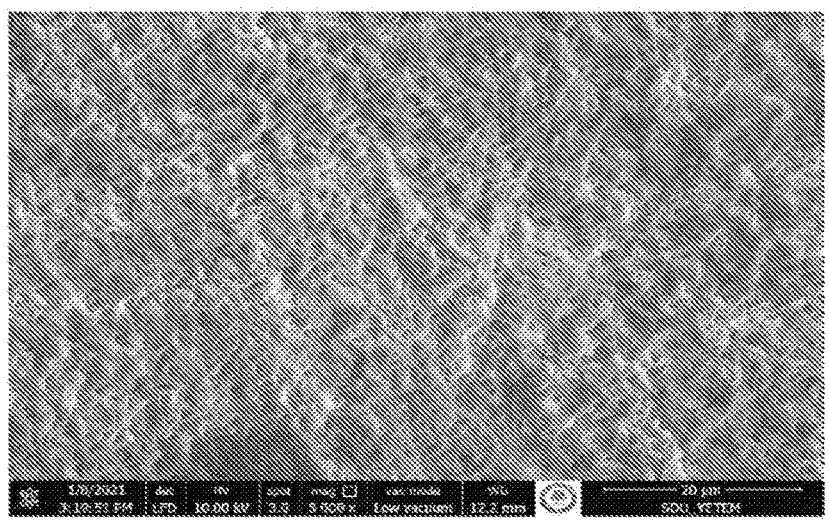
FIG. 24 is an SEM image of sandwich structures after release study for sample USP0.7-30 (×5000), according to at least one embodiment of the present invention.
Figure 25:
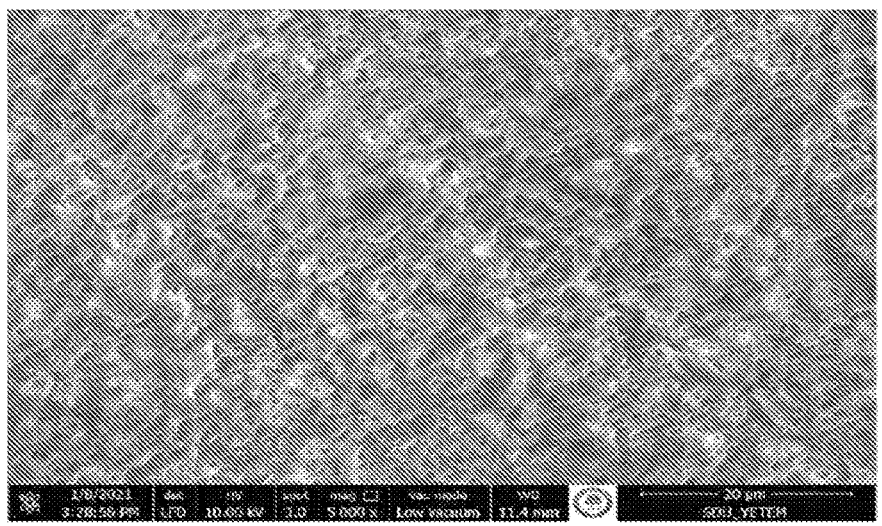
FIG. 25 is an SEM image of sandwich structures after release study for sample USP0.7-45 (×5000), according to at least one embodiment of the present invention.
Figure 26:
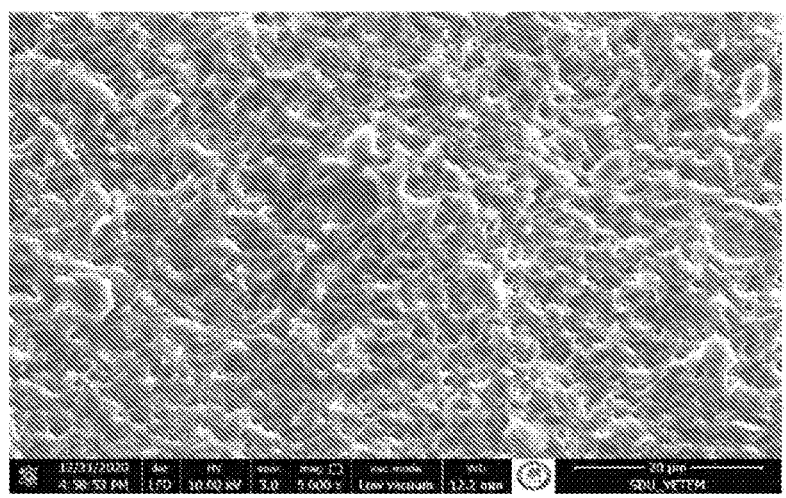
FIG. 26 is an SEM image of sandwich structures after release study for sample USP0.7-60 (×5000), according to at least one embodiment of the present invention.

FIG. 14 shows the cumulative release graphs of nanofiber surfaces coated with different amounts of AZI by the USP method.

In the USP technique, the model drug AZI is coated on the surface of the nanofibers. Therefore, when the drug-loaded nanofibers were taken into the dissolution medium, they diffused very quickly and the loaded drug was suddenly released as expected. It has been observed that the surfaces generally release fast, but the AZI concentration has no effect on the release. All samples released all loaded AZI within the first 30 minutes. It is clearly seen that drug delivery systems prepared by this method are also quite suitable for drugs that require immediate release.

Sandwich structures have been created to obtain systems that can release more slowly with the USP method. For this, 5 different pure PVP/GEL nanofibers produced for 1 hour were coated with USP, so as to contain 0.7% AZI, which was selected optimally in previous release studies. Then, PVP/GEL nanofiber production was carried out on these coated surfaces for 5 to 60 minutes (in the examples 5, 15, 30, 45 and 60 minutes were studied). The release profiles of these sandwich structures were investigated. In FIG. 15A-B, cross-section and surface SEM images of the sandwich structure, each layer of which is produced for 60 minutes (USP0.7-60), are provided.

Diameter, thickness, weight, and loading effect values of sandwich structures are given in Table 6.

TABLE 6

Diameter, weight, thickness, and loading effect values of sandwich structures

| Sample Code | Nano mesh diameter (mm) | Nano mesh thickness (μm) | Nano mesh weight (mg) | Loading effect (%) |
|---|---|---|---|---|
| USP0.7-5 | 64 | 311.2 | 47.5 | 87 |
| USP0.7-15 | 60 | 342.6 | 49.8 | 89 |
| USP0.7-30 | 69 | 628.1 | 52.8 | 94 |
| USP0.7-45 | 65 | 690.3 | 59.9 | 97 |
| USP0.7-60 | 68 | 719.8 | 68.9 | 98 |

When FIG. 16 is examined, it can be clearly stated that the nanofiber sandwich structure has been successfully obtained. A very small amount of bead structure seen on the surface was also revealed in the cross-sectional image. In the surface image, it was again revealed that the nanofibers are quite thin and smooth. The release profiles of these sandwich structures are provided in FIG. 16.

When Table 6 and FIG. 16 are analyzed, it is seen that as the thickness of the sandwich structures formed increases, the release time also prolongs. Because, in these structures, the drug is located only in the middle layer. There are no drugs on the surface and near the surface of the sandwich structures. Therefore, drug molecules could not diffuse into the dissolution medium quickly. It was determined that the release time increased from 30 minutes to 2 hours when nanofibers were produced on the drug layer coated with USP for a short time such as 5 minutes, and it extended up to 2 days when it was produced for 1 hour. While S0.7 sample with the same amount of drug loading without creating a sandwich structure released 80% of the loaded drug in the first 30 minutes, it released 22.15% when the sandwich was formed for 5 minutes, and only 9.38% when the sandwich structure was formed for 60 minutes.

In release studies with USP, by means of this method, it has been shown that drug delivery systems that can be used not only in situations where immediate release is desired can be prepared, but also that long-term release systems can be created by trapping drug molecules in the middle of the sandwich structure. As a result of drug release studies with this method, it has been seen that drug delivery systems that can both immediate release and slow release can be created by using the same method, the same polymer concentrations, and the same amount of drug. The creation of systems according to the desired release feature with a single method makes this method advantageous.

When FIGS. 17-21 are examined, it is seen that the fibrous structures of the surfaces are highly deformed compared to the conventional electro-spinning method. The reason for this is thought to be due to the fact that the coating process was made directly on the surface and the images were taken from these surfaces. However, it is noteworthy that with the increasing amount of coating, the surfaces tend to preserve their porous structure. Considering that there is a 9-fold difference between the lowest concentration and the highest concentration and the release times are very close to each other, this situation is thought to occur due to the fact that there is not enough time for the AZI-coated pores to empty with passage of high concentrations of AZI molecules to the dissolution medium during uptake, and due to the fact that there is not enough time for swelling since the release time is also fast.

Post-release SEM images of sandwich structures are provided in FIGS. 22-26. From the SEM images given, it is observed that the pores in the sandwich structures are considerably smaller or disappear. It was concluded that the reason for such distortion of the nanofibrous and porous structure was due to the considerable swelling of the fibers during the long release period.

The invention claimed is:

1. A production method of drug-loaded, PVP/GEL-based, nanofiber medical textile surfaces that can provide transdermal drug delivery as burst or controlled release, the method comprising:
   a) preparing polymer solutions containing PVP (polyvinylpyrrolidone) with a concentration of 12 wt % and GEL (gelatin) with a concentration of 0.72 wt %,
   b) producing nanofibers from the prepared polymer solutions by atmosphere-controlled horizontal needle fiber spinning of an electrospinning set up,
   c) obtaining PVP/GEL nanofibers by performing a cross-linking process of the produced nanofibers in two steps to maintain the stability of the produced nanofibers in aqueous environments, and
   d) coating a drug active substance as a thin film on the obtained PVP/GEL nanofibers by USP (ultrasonic spray pyrolysis) method.

2. The production method according to claim 1, wherein the producing nanofibers further comprises: fiber spinning at 26.4 kV voltage, 0.3 mL/h feed rate, with a distance of 17.0 cm between electrodes of the set up, a needle diameter of 0.8 m, 33±2% humidity, and at 23.5±1° C. temperature for 60 minutes.

3. The production method according to claim 2, further comprising:
   providing a slow release system by:
   coating the PVP/GEL nanofibers for 1 hour by said USP with 0.7% azithromycin (AZI), and
   producing additional PVP/GEL nanofibers in a sandwich structure on the coated surfaces for 5 to 60 minutes.

4. The production method according to claim 1, wherein the coating the drug active substance further comprises: coating with the PVP/GEL nanofibers arranged on a substrate having a temperature of 100° C., with a flow rate of 1 mL/min, a coating nozzle frequency of 85 kHz, a distance between the nozzle and the substrate of 13 cm, and a forming nitrogen gas pressure of 1 kPA.

5. The production method according to claim 1, wherein the performing the cross-linking further comprises:
   first crosslinking PVP polymer of the produced nanofibers at 180° C. for 4 hours, and
   then chemically cross-linking GEL polymer of the produced nanofibers with a glutaraldehyde crosslinker.

6. The production method according to claim 1, wherein the coating the drug active substance further comprises:
   providing a slow-release system by:
   dissolving the drug active substance of the drug azithromycin (AZI) in chloroform,
   adding n-hexane as an anti-solvent to the solution to prevent the chloroform from dissolving a surface of the PVP/GEL nanofibers,
   adjusting the chloroform: n-hexane ratio in the solution to 1:5, and
   adjusting the concentration of the drug active substance to 0.3 mg/mL.

7. The production method according to claim 6, wherein an amount of the AZI/chloroform/n-hexane solution coated on the PVP/GEL nanofibers is between 942 and 8460 μL.

8. The production method according to claim 1, wherein a diameter of nano meshes of the PVP/GEL nanofibers coated with said USP is 51-52 mm, a thickness of the nano meshes is 332.3-374.3 μm, and a weight of the nano meshes is 45.2-43.5 mg.

9. The production method according to claim 1, wherein a diameter of nano meshes of the PVP/GEL nanofibers coated with said USP is 51-52 mm, a thickness of the nano meshes is 311.2-719.8 μm, and a weight of the nano meshes is 45.2-43.5 mg.

* * * * *